US005749868A

United States Patent [19]

Furumoto

[11] Patent Number: 5,749,868
[45] Date of Patent: May 12, 1998

[54] NEAR INFRA-RED SELECTIVE PHOTOTHERMOLYSIS FOR ECTATIC VESSELS AND METHOD THEREFOR

[75] Inventor: Horace W. Furumoto, Wellesley, Mass.

[73] Assignee: Cynosure, Inc., Chelmsford, Mass.

[21] Appl. No.: 720,267

[22] Filed: Sep. 26, 1996

Related U.S. Application Data

[63] Continuation of Ser. No. 353,565, Dec. 9, 1994.
[51] Int. Cl.$^6$ .................................................... A61N 5/06
[52] U.S. Cl. ................................. 606/9; 606/3; 606/13
[58] Field of Search ........................ 606/2, 3-18; 604/20; 600/108

[56] References Cited

U.S. PATENT DOCUMENTS

| | | |
|---|---|---|
| 4,122,853 | 10/1978 | Smith . |
| 4,829,262 | 5/1989 | Furumoto . |
| 5,006,293 | 4/1991 | Furumoto . |
| 5,009,658 | 4/1991 | Damgaard-Iversen et al. . |
| 5,057,104 | 10/1991 | Chess . |
| 5,066,293 | 11/1991 | Furumoto .................... 606/9 |
| 5,071,416 | 12/1991 | Heller et al. . |
| 5,287,380 | 2/1994 | Hsia . |
| 5,290,273 | 3/1994 | Tan .............................. 606/3 |
| 5,304,167 | 4/1994 | Freiberg ........................ 606/3 |
| 5,344,418 | 9/1994 | Ghaffari . |
| 5,405,368 | 4/1995 | Eckhouse . |
| 5,558,667 | 9/1996 | Yarborough et al. ........... 606/9 |

FOREIGN PATENT DOCUMENTS

| | | |
|---|---|---|
| 0 297 360 A1 | 1/1989 | European Pat. Off. . |
| 0 413 025 A1 | 2/1991 | European Pat. Off. . |
| 91/13652 | 9/1991 | WIPO . |
| 91/13653 | 9/1991 | WIPO . |
| WO 91/18646 | 12/1991 | WIPO . |
| WO 92/03977 | 3/1992 | WIPO . |
| WO 92/06739 | 4/1992 | WIPO . |
| WO 95/15725 | 6/1995 | WIPO ................ A61B 17/41 |

OTHER PUBLICATIONS

Anderson, R.R., et al., "Selective Photothermolysis: Precise Microsurgery by Selective Absorption of Pulsed Radiation," *Science*, 220:524–527, Apr. (1983).

Anderson, R.R., et al., "Microvasculature Can Be Selectively Damaged Using Dye Lasers: A Basic Theory and Experimental Evidence in Human Skin," *Lasers in Surgery and Medicine* 1:263–276 (1981).

Anderson, R.R., et al., "The Optics of Human Skin," *The Journal of Investigative Dermatology*, 77(1):13–19 (1981).

"American Society for Laser Medicine and Surgery Abstracts," *Lasers in Surgery and Medicine*, Supplement 6, p. 46 (1994).

Anderson, R.R., "A Critical Look at Selective Photothermolysis—What is Known, What is Not, and What is Needed," Plenary Speech at American Society for Laser Surgery and Medicine, (Apr. 18–20, 1993).

"Selective Photothermolysis—The Candela Vascular Lesion Laser," *Candela*, Jun. 1990.

"Lumatec Liquid Lightguides," *Laser Focus World*, p. 116 (Jun. 1994).

"PhotoTome 50," Cynosure™, Inc., Bedford, Massachusetts, Advertising Brochure (No Date Given).

*Primary Examiner*—David Shay
*Attorney, Agent, or Firm*—Hamilton, Brook, Smith & Reynolds, P.C.

[57] ABSTRACT

Near-infrared selective photothermolysis for the treatment of ectatic blood vessels, for example, blood vessels of a portwine stain birthmark. This technique is especially applicable to deeper lying blood vessels in view of the better penetration of the near infrared light. Consequently, vessels are below a dermal/epidermal boundary can be reached. Near-infrared is defined as a range of approximately 700 to 1,200 nm. The optimal colors are near 760 or between 980 to 990 nm for most populations.

34 Claims, 2 Drawing Sheets

NEAR INFRA-RED SELECTIVE PHOTOTHERMOLYSIS FOR ECTATIC VESSELS AND METHOD THEREFOR

RELATED APPLICATION

This application is a continuation of co-pending application Ser. No. 08/353,565 filed on Dec. 9, 1994, which is incorporated herein by reference in its entirety.

BACKGROUND OF THE INVENTION

Vascular lesions, comprising enlarged or ectatic blood vessels, pigmented lesions, and tattoos have been successfully treated with lasers for many years. In the process called selective photothermolysis, the targeted structure, the lesion tissue or tattoo pigment particles, and the surrounding tissue are collectively irradiated with laser light. The wavelength or color of this laser light, however, is chosen so that its energy is preferentially absorbed into the target. Localized heating of the target resulting from the preferential absorption leads to its destruction.

Most commonly in the context of vascular lesions, such as portwine stains for example, hemoglobin of red blood cells within the ectatic blood vessels serves as the laser light absorber, i.e., the chromophore. These cells absorb the energy of the laser light and transfer this energy to the surrounding vessels as heat. If this occurs quickly and with enough energy, the surrounding vessels reach a temperature to denature their proteins. The fluence, Joules per square centimeter, to reach the denaturation of the vessels is calculated to be that necessary to raise the temperature of the targeted volume within the vessel to about 70° C. before a significant portion of the absorbed laser energy can diffuse out of the vessel. The fluence must, however, be limited so that the surrounding tissue is not also denatured.

As suggested, simply selecting the necessary fluence is not enough. The intensity and pulse duration of the laser light must also be optimized for selectivity by both minimizing diffusion into the surrounding tissue during the pulse while avoiding localized vaporization. Boiling and vaporization are desirably avoided since they lead to mechanical, rather than chemical, damage—which can increase injury and hemorrhage in tissue surrounding the lesion. These constraints suggest that the pulse duration should be longer with a correspondingly lower intensity to avoid vaporization. Because of thermal diffusivity, energy from the laser light pulse must be deposited quickly, however, to minimize heat dissipation into the surrounding tissue. The situation becomes more complex if the chromophore is the blood cell hemoglobin within the lesion blood vessels, since the vessels are an order of magnitude larger than the blood cells. Radiation must be added at low intensities so as to not vaporize the small cells, yet long enough to heat the blood vessels by thermal diffusion to the point of denaturation and then terminated before tissue surrounding the blood vessels is damaged.

Conventionally, long pulse flashlamp excited dye lasers have been used as the laser light source. These lasers have the high spectral brightness required for selective photothermolysis and can be tuned to the alpha absorption band of hemoglobin. Colors in the range of 577 to 585 nm are absorbed well by the chromophore, the red blood cells in the blood vessels. Further, the relative absorption between the targeted blood and the melanin in the surrounding tissue is optimum in order to minimize heating of the melanin.

SUMMARY OF THE INVENTION

The implementation of dye lasers tuned to the conventional color range presents a number of drawbacks. Theory dictates that the length of the light pulse should be on the order of the thermal relaxation time of the ectatic vessels. Larger ectatic vessels, greater than 30 microns, consequently require pulse durations of 0.5 msec and longer. Commercially available dye lasers are limited in pulse durations to approximately 0.5 msec and shorter, however. Further, current research suggests that pulse durations exceeding 0.7 msec are probably not attainable by these lasers. As a result, in selective photothermolysis treatment of these larger ectatic vessels, higher than optimum fluences must be used to compensate for the pulse duration limitations. This leads to temporary hyperpigmentation, viz., purpura. Moreover, the molar extinction coefficient, a measure of a chemical's optical absorption characteristics, is approximately 0.2 for both melanin and hemoglobin in the range of 577 to 585 nm. As a result, for fair Caucasian skin, for example, the effective penetration depth of light in this wavelength range is limited to less than 0.5 mm. Therefore, the dye laser treatment techniques work exceptionally well on vascular lesions comprised of vessels less than 30 microns in diameter and located above the dermal/epidermal junction. On the negative side, deep penetration is limited because of the high absorption, and multiple treatments are necessary to get at deeper vessels. Further, as previously noted large vessels are sub-optimally treated with pulses that are too short in time.

The near infra-red portion of the electro-magnetic spectrum, designated for the purposes of this description as stretching from approximately 700 to 1200 nm, provides regions of favorable ratios between competing melanin and hemoglobin absorption. The use of these wavelengths for the treatment of ectatic blood vessels has been universally ignored as an alternative to the 577–585 nm wavelengths because of the poor hemoglobin absorption characteristics in this area. This conclusion, however, fails to recognize that the ratio between the absorption characteristics of the hemoglobin and the melanin is the principle variable in achieving selectivity, not net absorption. Moreover, in the treatment of deeper lying vessels, the poor absorption characteristics can actually be an asset since it enables deeper overall penetration of the laser light.

In light of the above, in general, according to one aspect, the invention is directed to near-infrared selective photothermolysis for the treatment of vascular lesions. In specific embodiments, this technique is used to treat ectatic blood vessels, for example, blood vessels of a portwine stain birthmark. This technique is especially applicable to deeper lying blood vessels in view of the better penetration of the near infrared light. Consequently, vessels below a dermal/epidermal boundary can be reached.

In specific embodiments a few different wavelength ranges are possible. Generally, the near-infrared light is in the range of approximately 700 to 1,200 nm. More specifically, the range can be limited to 750 to 780 nm. The best color is 760 nm, however. Alternatively, a general range of 980 to 990 nm is also effective.

The laser light is preferably generated by one of an alexandrite, titanium sapphire, chromium doped fluoride, or semiconductor diode laser and conveyed to the patient via an optical fiber delivery system for transmitting the laser light to a patient.

In general according to another aspect, the invention features a near-infrared selective photothermolysis device for treatment of ectatic vascular lesions. This device comprises a laser system for generating near-infrared laser light pulse having a duration of greater than 0.2 milliseconds and a delivery system for transmitting the laser light pulse to a patient.

In specific embodiments, the laser system includes an alexandrite, titanium sapphire, chromium doped fluoride, or semi-conductor diode-type laser. If the pulse duration or power output of the selected laser is inadequate individually, the light pulses from multiple diode lasers, for example, can be combined. Time-multiplexing achieves long effective pulse durations. Consequently, effective pulse durations of between 1 and 10 msec are achievable when individual laser diodes only produce pulses of 0.5 msec. Combinations of simultaneously generated beams increase effective power.

In general according to still another aspect, the invention features a method for treating a vascular lesion. This method comprises irradiating the lesion with near-infrared laser light pulses. The duration of these pulses is controlled to approximately match a thermal relaxation time of blood vessels of the lesion. The near-infrared wavelengths stretch from approximately 700 to 1,200 nm.

The above and other features of the invention including various novel details of construction and combinations of parts, and other advantages, will now be more particularly described with reference to the accompanying drawings and pointed out in the claims. It will be understood that the particular method and device embodying the invention is shown by way of illustration and not as a limitation of the invention. The principles and features of this invention may be employed in various and numerous embodiments without the departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
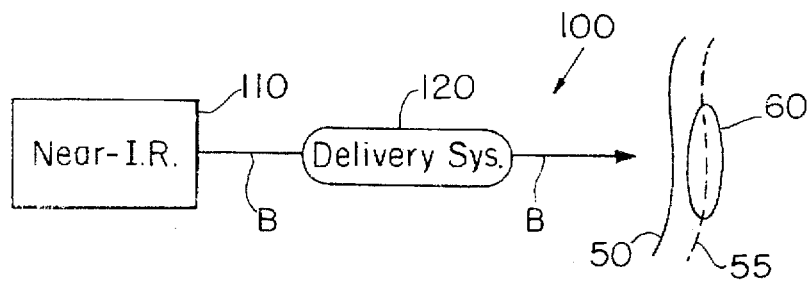
FIG. 1 schematically shows a near-infrared selective photothermolysis device of the invention using a single laser.

Turning now to the drawings, a near-infrared selective photothermolysis device 100, constructed according to the principles of the present invention, is illustrated in FIG. 1. This device 100 is generally similar to that found in the prior art except to the extent that it includes a radiation source that generates light pulses in the near-infrared region of the electromagnetic spectrum. More completely, a laser system 110 generates a beam of near-infrared light B, i.e., in the range of 700-1200 nm. The beam of light B is coupled into a delivery system 120, such as a single optical fiber, and transported to the skin 50 of a patient. Because this light beam B is in the near-infrared region of the spectrum, it can achieve substantial penetration beyond a dermal/epidermal boundary 55 to treat an entire portion of a vascular lesion 60.

This lesion 60 could be of one of many different types such as portwine stain birthmarks, hemangiomas, telangiectasia, idiopathic vulvodynia, and leg veins. Further, it could also be vessels in simple wrinkles, caused by age or sun exposure, or blood vessels in scar tissue.

The pulse duration of the light beam B is matched to the thermal relaxation time of the targeted ectatic vessels. Generally, this requires durations greater than 0.2 msec. For vessels of 30 microns in diameter and larger, as are present in portwine stains of adult patients, the duration should ideally exceed 0.5 msec, whereas pulse durations of 1 msec to 10 msec should be selected, if the vessels are larger than 100 microns.

Figure 2:
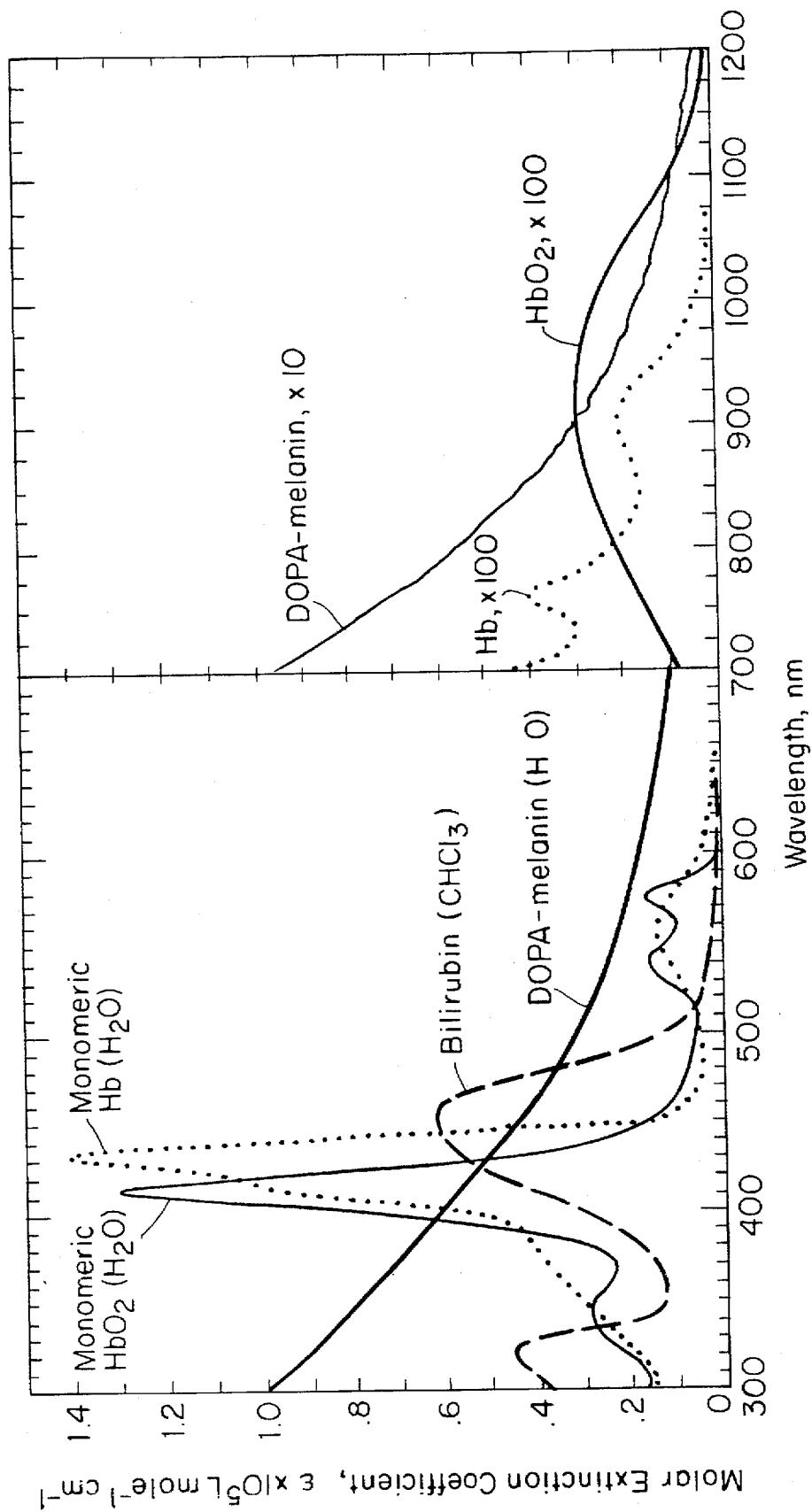
FIG. 2 is a plot of the molar extinction coefficient as a function of wavelength, in nanometers, for oxyhemoglobin $HbO_2$ (solid line), deoxyhemoglobin Hb (dotted line), bilirubin (dashed line), and DOPA-melanin (the apparently exponentially falling solid line)

Referring to FIG. 2, there are a number of specific ranges within the near-infrared that will be especially effective in treating vascular lesions. (Because the molecular weights of melanin are poorly defined, the spectrum shown is the optical density on a scale of 0 to 1.5 for a 1.5 mg % solution of DOPA-melanin.) FIG. 2 is a plot of the molar extinction coefficient as a function of wavelength in nanometers.

For an acceptable degree of selectivity in fair Caucasian skin, the ratio between the molar extinction coefficient of the hemoglobin and the melanin should be at least 0.05. The ratio of combined deoxyhemoglobin (Hb) and oxyhemoglobin ($HbO_2$) absorption to melanin absorption (DOPA-melanin) is generally favorable, 0.05 or greater, between 700 and 1,200 nm. If the deoxyhemoglobin Hb is specifically targeted, the wavelength range of 700 to 1,000 nm of the laser beam B is acceptable. The deoxyhemoglobin absorption peaks in the range of 750 to 780 nm with the best ratios at approximately 760 nm.

The total absorption of hemoglobin is less in the near-infrared than the conventional range of 577–585 nm. Therefore, fluences of the light beam B required to treat ectatic vessels are higher than fluences used with conventional shorter wavelengths. Therefore, the light beam B generally provides fluences of between 2 and 20 $J/cm^2$.

The laser system 110 can comprise several candidate lasers, which are available to generate the near-infrared laser light around 760 nm. For example, alexandrite is tunable within the range of 720–790 nm. Also tunable titanium sapphire (TiS) produces light in the range of 720–950 nm. These two lasers appear to be the best candidates since they are highly developed under current technology. Other tunable chromium doped fluoride lasers such as $LiCaAlF_6$, $LiCaGaF_6$, $LiSrAlF_6$, and $LiSrGaF_6$ in addition to semiconductor diode lasers are also potential alternatives.

Alexandrite lasers are particularly well adapted to selective photothermolysis since pulse generation in the range of 3 to 10 msec is possible. This pulse duration is most appropriate for the treatment of ectatic vessels of 100 microns and larger, which are ineffectively treated by currently available technology. These lasers, however, exhibit a very spiky behavior in the so-called normal mode of operation. This results from relaxation oscillation.

Figure 3:
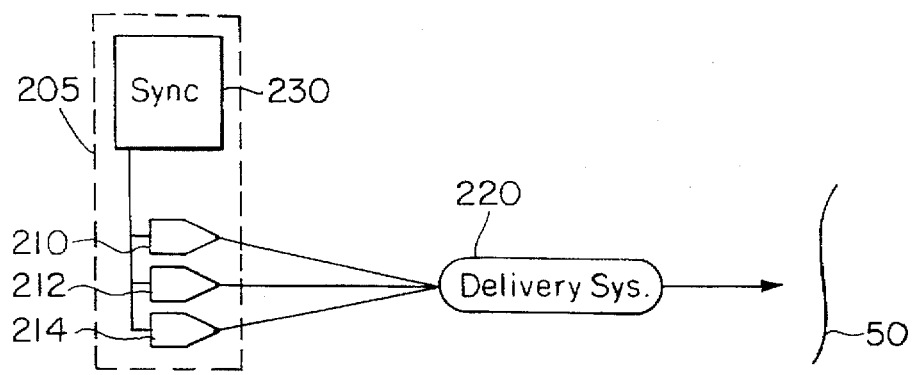
FIG. 3 schematically shows a near-infrared selective photothermolysis device of the invention using multiple laser diodes or diode arrays.

Semiconductor diode lasers do not store energy in a metastable upper laser level and consequently do not show the spiky behavior. The individual power output is, however, too low to reach the necessary fluences which are necessary to treat ectatic vessels. Implementation of diode lasers requires the combination of beams from many lasers to reach the more than 100 watts needed. Such an embodiment is schematically shown in FIG. 3 in which the outputs from three diode lasers 210, 212, 214 of the laser system 205 are combined into a single beam and coupled into the delivery system 220. The diode lasers 210–214, or TiS lasers, are coordinated by a synchronizer 230 that controls their respective times of light generation. Alternatively, if still more power is required the diode lasers 210, 212, 214 are alternatively replaced with separate arrays of diodes. In either case, the delivery system 220 is a liquid core flexible light guide instead of a single glass optical fiber. These liquid core guides have large apertures, typically 5 mm and still retain flexibility. Thus, beams from the several diode lasers, or several arrays, are directly focused onto the liquid light guide, greatly simplifying the transfer optics between the laser diodes and the ectatic vessels.

Another device for combining many beams from diode lasers is specifically disclosed in U.S. patent application Ser. No. 08/163,160, entitled, "Fault Tolerant Optical System Using Diode Laser Array," of which the present inventor is a co-inventor and which is incorporated herein by this reference. This application is directed to the use of corrective micro-optics to mate a two-dimensional diode array with a masked-produced two-dimensional array of collimator micro-lens and mass-produced transformer sets.

Figure 4:
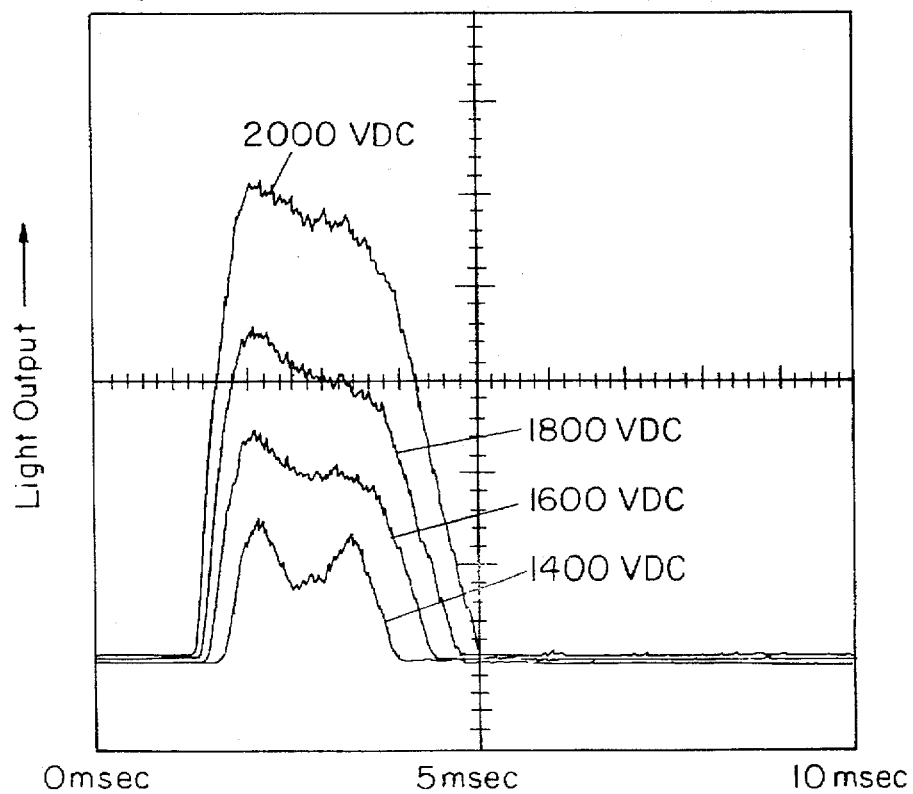
FIG. 4 is a plot of TiS laser output as a function of time for different levels of flashlamp excitation, showing that relaxation oscillation is not a factor for long pulse durations.

The TiS laser is another viable candidate. In tests, these lasers have produced 1 to 5 msec pulses and did not exhibit the spiky behavior that is characteristic of flashlamp excited solid state laser systems. Most solid state lasers have an upper state lifetime of approximately 100 μsec. In the TiS laser, however, this lifetime is only 3 μsec. As a result, if the TiS lasing medium is pumped hard, as for example how dye lasers are pumped, the upper state becomes saturated and will not store any more energy after about 2–3 μsec. This neutralizes most relaxation oscillation pulsing. For example, as shown in FIG. 4, four different levels of flashlamp excitation are demonstrated, 2,000, 1,800, 1,600, and 1400 V.D.C. The resulting pulse durations of two to three msec do not exhibit strong relaxation oscillation pulsing characteristics. The pulses tended to be limited in duration to approximately 3 msec, however, by thermal lensing effects.

If individual TiS lasers are not capable of producing the necessary pulse durations, the laser system 110 of FIG. 3 may time multiplex the outputs of several lasers as taught in U.S. patent Ser. No. 08/329,195, filed on Oct. 26, 1994, entitled "Ultra Long Pulsed Dye Laser for Treatment of Ectatic Vessels and Method Therefor," of which the present inventor is a co-inventor and which is incorporated herein by this reference. Specifically, the synchronizer 230 of FIG. 3 sequentially triggers each of the diode or TiS lasers 210–214 to thereby generate effective pulse durations. Alternatively or additionally, to achieve high effective power output, the synchronize 230 simultaneously triggers all of some of the lasers 210–214.

The deoxyhemoglobin $HbO_2$ can be specifically targeted, which has a favorable absorption range between 800 and 1200 nm. The best absorption ratios exist between 980 and 990 nm. Here, the molar extinction coefficient of the oxyhemoglobin $HbO_2$ peaks and the coefficient ratio of oxyhemoglobin to melanin actually exceeds 0.1. This is a desirable range for diode laser treatment. 50 watt fiber coupled continuous wave diode lasers, stand alone and fully developed, are commercially available. These state of the art diode laser arrays can produce 100 watts in a quasicontinuous wave mode. The pulse duration of these modes is typically around 400 μsec. Therefore, in the treatment of larger ectatic vessels time-multiplexed arrays of diode lasers, as described above, are necessary.

While this invention has been particularly shown and describe with references to preferred embodiments thereof, it will be understood by those skilled in the art that various changes in form and details may be made therein without departing from the spirit and scope of the invention as defined by the appended claims.

I claim:

1. A near-infrared selective photothermolysis device for treatment of vascular targets, the device comprising:
   a laser system for generating near-infrared laser light pulses having wavelengths in a range of approximately 750 to 780 nm and durations that concentrate heat from the light pulses in the vascular targets and selectively damage the vascular targets; and
   a delivery system for receiving the laser light pulses from the laser system and transmitting the laser light pulses to the vascular targets of a patient.

2. A device as claimed in claim 1, wherein the laser light pulses have a wavelength in a range of approximately 760 nm.

3. A device as claimed in claim 1, wherein the laser system comprises an Alexandrite laser.

4. A device as claimed in claim 1, wherein the laser system comprises a titanium sapphire laser.

5. A device as claimed in claim 1, wherein the laser system comprises a semi-conductor diode laser.

6. A device as claimed in claim 1, wherein the laser system comprises plural lasers.

7. A device as claimed in claim 6, wherein the delivery system comprises an optical fiber for combining and delivering light from the lasers.

8. A device as claimed in claim 6, wherein the laser system simultaneously triggers the lasers to increase effective power levels.

9. A device as claimed in claim 6, wherein the laser system further comprises a synchronizer for time-multiplexing the lasers.

10. A device as claimed in claim 9, wherein a total duration of light pulses from the time-multiplexed lasers is between 1 and 10 msec.

11. A near-infrared selective photothermolysis device for treatment of vascular targets, the device comprising:
    a laser system for generating near-infrared laser light pulses having wavelengths in a range of approximately 980 to 990 nm and durations that concentrate heat from the light pulses in the vascular targets and selectively damage the vascular targets; and
    a delivery system for transmitting the laser light pulses to the vascular targets of a patient.

12. A device as claimed in claim 11, wherein the laser system comprises a chromium doped fluoride laser.

13. A method for performing selective photothermolysis, comprising:
    generating near-infrared laser light in the range of 750 to 780 nm; and
    treating vascular targets with the laser light.

14. A method as claimed in claim 13, further comprising generating the laser light with a pulse duration of greater than 0.2 milliseconds.

15. A method as claimed in claim 13, further comprising generating the laser light with a pulse duration within a range of 1 to 10 milliseconds.

16. A method as claimed in claim 13, further comprising generating the laser light with a wavelength of approximately 760 nm.

17. A method as claimed in claim 13, further comprising treating blood vessels below a dermal/epidermal boundary.

18. A method as claimed in claim 13, further comprising generating the laser light with an alexandrite laser.

19. A method as claimed in claim 13, further comprising generating the laser light with a titanium sapphire laser.

20. A method as claimed in claim 13, further comprising transmitting the laser light to the vascular target of a patient with an optical fiber delivery system.

21. A method as claimed in claim 13, further comprising treating leg veins with the laser light.

22. A method as claimed in claim 13, further comprising treating ectatic blood vessels of vascular lesions with the laser light.

23. A method as claimed in claim 22, further comprising treating ectatic blood vessels of a portwine stain birthmark.

24. A method for performing selective photothermolysis, comprising:

generating near infrared laser light in the range of approximately 980 to 990 nm; and treating vascular targets with the laser light.

25. A method as claimed in claim 24, further comprising treating leg veins with the laser light.

26. A method as claimed in claim 24, further comprising generating the laser light with a chromium-doped fluoride laser.

27. A method as claimed in claim 24, further comprising generating the laser light with a semiconductor diode laser.

28. A method as claimed in claim 24, further comprising generating the laser light with a pulse duration of greater than 0.2 milliseconds.

29. A method as claimed in claim 24, further comprising generating the laser light with a pulse duration within a range of 1 to 10 milliseconds.

30. A method as claimed in claim 24, further comprising treating blood vessels below a dermal/epidermal boundary.

31. A method as claimed in claim 24, further comprising treating ectatic blood vessels of vascular lesions with the laser light.

32. A method as claimed in claim 31, further comprising treating ectatic blood vessels of a portwine stain birthmark.

33. A method for performing selective photothermolysis on vascular targets, the method comprising:

irradiating the targets with near-infrared laser light pulses having wavelengths in a range of 750 to 780 nm; and controlling a duration of the pulses to concentrate heat from the light pulses in the vascular targets and selectively damage the vascular targets.

34. A method for performing selective photothermolysis on vascular targets, the method comprising:

irradiating the targets with near-infrared laser light pulses having wavelengths in a range of 980 to 990 nm; and controlling a duration of the pulses to concentrate heat from the light pulses in the vascular targets and selectively damage the vascular targets.

* * * * *